(12) United States Patent
Patil et al.

(10) Patent No.: US 9,250,154 B1
(45) Date of Patent: Feb. 2, 2016

(54) SYSTEMS AND METHODS FOR DETECTING LIGHT LEAKAGE IN A DEVICE

(71) Applicant: Amazon Technologies, Inc., Reno, NV (US)

(72) Inventors: Prashanth Basavaraj Patil, Santa Clara, CA (US); Scott Michael Dylewski, San Francisco, CA (US); Yan Karasik, Sunnyvale, CA (US)

(73) Assignee: Amazon Technologies, Inc., Reno, NV (US)

( * ) Notice: Subject to any disclaimer, the term of this patent is extended or adjusted under 35 U.S.C. 154(b) by 0 days.

(21) Appl. No.: 14/315,621

(22) Filed: Jun. 26, 2014

(51) Int. Cl.
| | |
|---|---|
| G01J 1/00 | (2006.01) |
| G01M 11/00 | (2006.01) |
| G01N 21/95 | (2006.01) |
| G01J 1/42 | (2006.01) |
| G01M 3/38 | (2006.01) |

(52) U.S. Cl.
CPC ........ *G01M 11/00* (2013.01); *G01J 1/42* (2013.01); *G01M 3/38* (2013.01); *G01N 21/95* (2013.01); *G01N 2201/125* (2013.01)

(58) Field of Classification Search
CPC .......... G02B 1/04; G02B 5/3016; G02B 1/08; G02B 1/12; G02B 27/0093; G02B 27/2214; G02B 27/225; G02B 5/30; G02B 5/3033; G02B 5/3083; G02B 6/0045; G02B 6/0046; G02B 6/0048; G02B 6/0068; G02B 6/0073
See application file for complete search history.

(56) References Cited

U.S. PATENT DOCUMENTS

| | | | | |
|---|---|---|---|---|
| 4,213,703 | A | * | 7/1980 | Haunold et al. .............. 356/244 |
| 2013/0242290 | A1 | * | 9/2013 | Yin et al. ...................... 356/218 |
| 2014/0214367 | A1 | * | 7/2014 | Tong ............................. 702/189 |

* cited by examiner

*Primary Examiner* — Michael P Stafira
(74) *Attorney, Agent, or Firm* — Sutherland Asbill & Brennan LLP (57) ABSTRACT

According to one or more embodiments of the disclosure, a testing apparatus is provided. The testing apparatus may include a base portion configured to receive a device under test (DUT). The base portion may also include an array of light sensors to measure light leakage from the DUT. For example, the testing apparatus may receive, from the array of light sensors, one or more light intensity measurements associated with light leakage from between a bezel element and a display element along a first edge portion of the DUT. The testing apparatus may then transmit the measurements to a testing computer.

20 Claims, 8 Drawing Sheets

SYSTEMS AND METHODS FOR DETECTING LIGHT LEAKAGE IN A DEVICE

Mobile devices today may include a display portion coupled to a bezel portion. In some instances, the display portion may be improperly coupled to the bezel portion such that light emitted from backlight associated with the display may leak out of the device. Depending on its intensity, such light leakage may be aesthetically displeasing. Therefore, during the testing of such devices, a tester may be used to examine the devices for light leakage and to determine whether any such leakage is associated with too great a light intensity. Such an examination process may be relatively labor-intensive as well as subjective in nature.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers in the figures refer to like elements throughout. Hence, if a feature is used across several drawings, the number used to identify the feature in the drawing where the feature first appeared will be used in later drawings.

DETAILED DESCRIPTION

Described herein are systems and methods for testing light leakage, such as light leakage associated with a user device. For instance, a user device may include a display coupled to a bezel. In certain implementations, the display may be glued to the bezel although it will be appreciated that various other means of coupling the display to the bezel are also contemplated. Furthermore, the display may include a backlight and/or other lighting element to illuminate the display. In some cases, improper coupling between the display and the bezel and/or other similar defects may occur. As a result, light emanating from the backlight may leak out between the display and the bezel. Such light leakage may be aesthetically undesirable.

According to one or more embodiments, a testing device may be provided to detect and/or otherwise test for light leakage associated with a device under test (DUT) (e.g., the user device). In certain implementations, the testing device may be a clam shell apparatus although other shapes and structures are also contemplated. The testing device may include a base portion. The base portion may include a device receptacle component that may be configured to receive the DUT. Furthermore, one or more sensor arrays may be coupled to the base portion, such as along the outer edges of the device receptacle component. As a result, when the DUT is placed in, set in, and/or otherwise coupled to the device receptacle component, the sensor arrays may be positioned along one or more edge portions of the DUT. Moreover, the sensor arrays may be positioned a predetermined distance from one or more edge portions of the DUT.

To this end, the one or more sensor arrays may be configured to receive one or more light intensity measurements along the one or more edge portions of the DUT. Such measurements may be provided to a data acquisition component included in the testing device. Furthermore, in certain implementations, the data acquisition component may be configured to transmit the one or more light intensity measurements to a testing computer. The testing computer may be configured to determine whether the one or more light intensity measurements are greater than a predetermined light intensity threshold.

For instance, each sensory array included in the testing device may include light sensors. Each of the light sensors may be configured to generate and/or otherwise provide a respective light intensity measurement, and the respective light intensity measurements may be transmitted to the testing computer as part of the one or more light intensity measurements. As such, the testing computer may successively compare the respective light intensity measurements with the light intensity threshold. In certain implementations, if any of the respective light intensity measurements exceed the light intensity thresholds, the testing computer may generate a test failure indication. In other words, the testing computer may determine the presence of light leakage along one or more of the edge portions of the DUT. The testing computer may also be configured to determine, based least in part on the one or more light intensity measurements, a location of any light leakages with respect to the DUT.

According to some embodiments, the testing device may also include a lid member, which may be hinged and/or otherwise coupled to the base portion. The lid member may be configured to adjust the testing apparatus into an open and/or closed position. In the closed position, the lid member may be configured to cover the DUT to prevent ambient light from entering space occupied by the DUT and the sensor arrays. Additionally, in certain embodiments, the sensor arrays may be coupled to the lid member instead of and/or in addition to the base portion. The sensor arrays maybe coupled to the lid member such that when the testing device is in a closed position, the sensor arrays may be positioned opposite the one or more edge portions of the DUT.

Figure 1A:
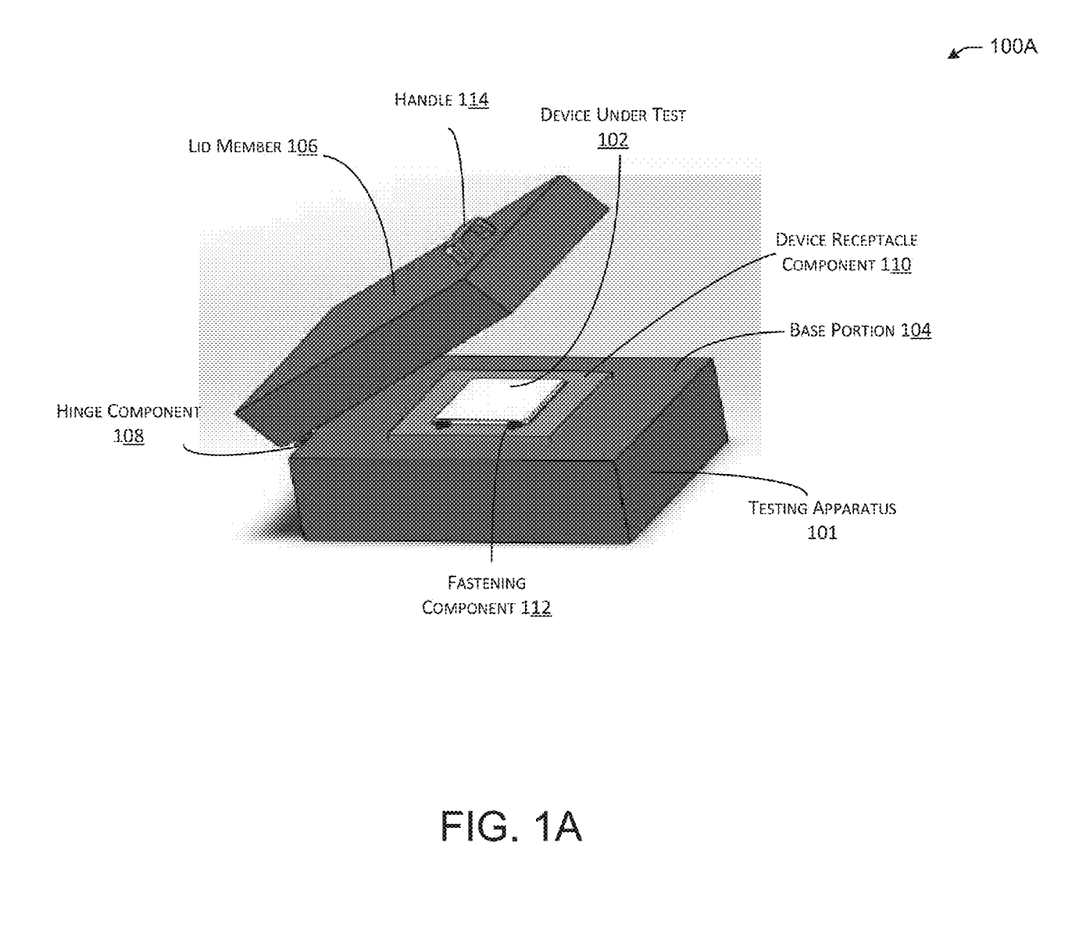
FIG. 1A illustrates a schematic diagram of a testing apparatus in accordance with one or more embodiments of the disclosure.

Referring now to FIG. 1A, a schematic diagram 100A of a testing apparatus 101 may be illustrated in accordance with one or more example embodiments. The testing apparatus 101 may include a base portion 104 and a lid member 106.

The lid member 106 may be pivotally coupled to the base portion 104 via one or more hinge components 108. As shown in FIG. 1A, the lid member 106 may be adjusted such that the testing apparatus 101 is in an open position. However, it will be appreciated that the lid member 106 may also be adjusted and/or otherwise brought down upon the base portion 104 to place the testing apparatus 101 in a closed position. While the testing apparatus 101 is in the closed position, the lid member 106 may cover a device-under-test (DUT) 102 to prevent ambient light in the environment from entering testing apparatus 101 and/or illuminating the DUT 102 (e.g., and thereby affect testing of the DUT 102). In general, the DUT 102 may refer to any type of electronic device, and more particularly, may refer to one or more of the following: a wireless communication device, a portable electronic device, a telephone (e.g., cellular phone, smart phone), a computer (e.g., laptop computer, tablet computer), a wearable computer device, a portable media player, a personal digital assistant (PDA), a television, or any other electronic device having a networked capability.

According to one or more embodiments, the testing apparatus 101 may also include a device receptacle component 110. The device receptacle component 110 may be configured to receive the DUT 102 (e.g., a tester may place the DUT 102 into or onto the device receptacle component 102). Furthermore, the DUT 102 may be secured in the device receptacle component 110 via one or more fastening components 112. The fastening components 112 may include, but are not limited to, spring contacts, rubber feet, foam inserts, and/or the like. In some implementations, a handle 114 may be coupled to the lid member 106 in order to facilitate adjustment of the testing apparatus 101 between the open position and the closed position.

Figure 1B:
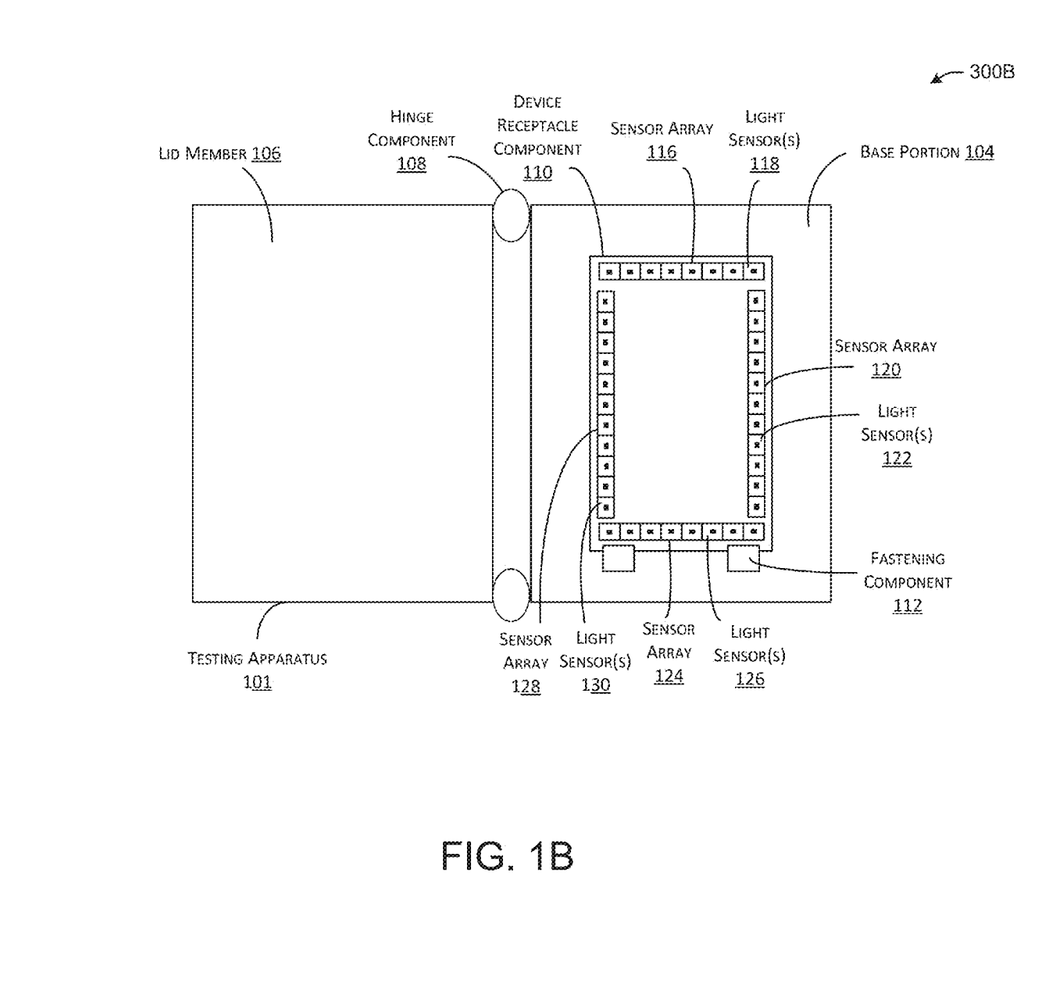
FIG. 1B illustrates another schematic diagram of the testing apparatus in accordance with one or more embodiments of the disclosure

FIG. 1B illustrates a schematic diagram 100B of the testing apparatus 101 in accordance with one or more example embodiments. The diagram 100B may show the testing apparatus 101 in an open position without the presence of the DUT 102. As depicted, one or more light sensor arrays (hereinafter sensor arrays) may be positioned within and/or otherwise coupled to the device receptacle component 110 along one or more edges of the device receptacle component 110. Additionally, each of the sensor arrays may include one or more light sensors coupled to each other.

For example, sensor array 116 may be positioned along the top edge portion of the device receptacle component 110 and may include one or more light sensors 118. Sensor array 120 may be positioned along the right edge portion of the device receptacle component 110 and may include one or more light sensors 122. Sensor array 124 may be positioned along the bottom edge portion of the device receptacle component 110 and may include one or more light sensors 126. Sensor array 128 may be positioned along the left edge portion of the device receptacle component 110 and may include one or more light sensors 130.

It will be appreciated that the number of sensor arrays 116, 120, 124, and 128 and light sensors 118, 122, 126, and 130 are for illustrative purposes only. The testing apparatus 101 may include a greater or fewer number of sensor arrays as desired. Furthermore, the sensor arrays may each include any number of light sensors. In addition, the sensor arrays 116, 120, 124, and 128 may be adjustable and/or rotatable along any axes and thereby positioned in any orientation. As such, the sensory arrays 116, 120, 124, and 128 may be configured to capture and/or otherwise obtain light intensity measurements from the DUT 102 at various angles with respect to the DUT 102.

Figure 1C:
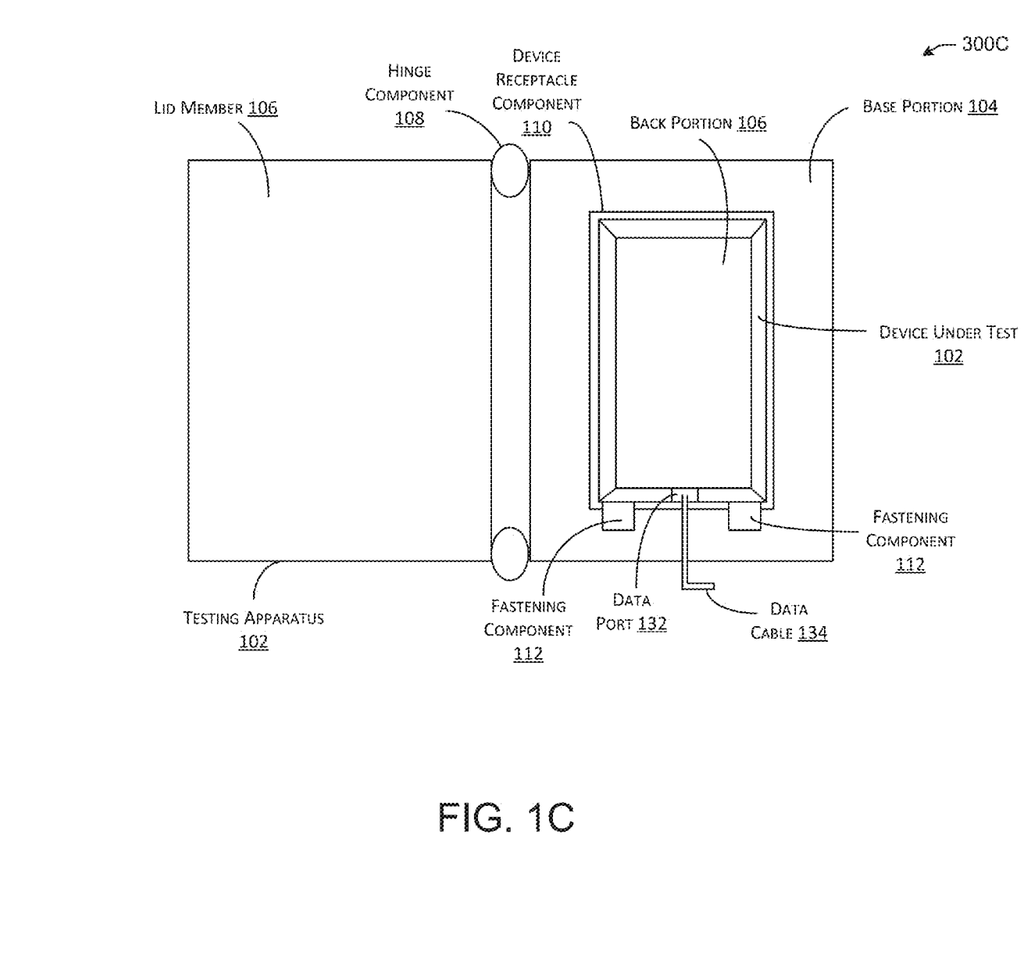
FIG. 1C illustrates another schematic diagram of the testing apparatus in accordance with one or more embodiments of the disclosure

FIG. 1C illustrates another schematic diagram 100C of the testing apparatus 101 in accordance with one or more example embodiments. The schematic diagram 100C may depict the testing apparatus 101 in an open position with the DUT 102 coupled to the device receptacle component 110.

According to certain embodiments, the DUT 102 may be placed face down on to the device receptacle component 110. As previously mentioned, the DUT 102 may be secured in place by one or more fastening components 112. In some implementations, the sensor arrays 116, 120, 124, and 128 may be configured to obtain light intensity measurements associated with different edge portions of the DUT 102. For instance, sensor array 116 may obtain light intensity measurements associated with light leakage along a top edge portion of the DUT 102. Sensor array 120 may obtain light intensity measurements associated with light leakage along a right edge portion of the DUT 102. Sensor array 124 may obtain light intensity measurements associated with light leakage along a bottom edge portion of the DUT 102. Sensor array 128 may obtain light intensity measurements associated with light leakage along a left edge portion of the DUT 102.

Additionally, the DUT 102 may include a data port 132 and a data cable 134 coupled to the data port 132. To this end, data associated with one or more light intensity measurements, as well as various other types of data (e.g., light sensor identifier information), may be transmitted via the data cable 134 to a testing computer (e.g., testing computer 518). According to certain embodiments, the data port 132 may be a USB port, and the data cable 134 may be a USB cable. It will be appreciated, however, that other types of data ports 132 and data cables 134 are also possible.

Furthermore, while FIG. 1C illustrates the DUT 102 as being placed face down on to the device receptacle component 110, in other implementations, the DUT 102 may be placed faced up on to the device receptacle component 110 (e.g., with the display 604 faced up). Furthermore, in such implementations, one or more of the sensor arrays 116, 120, 124, and 128 illustrated in FIG. 1B may be coupled to the lid member 106 instead of or in addition to the base portion 104.

Figure 2:
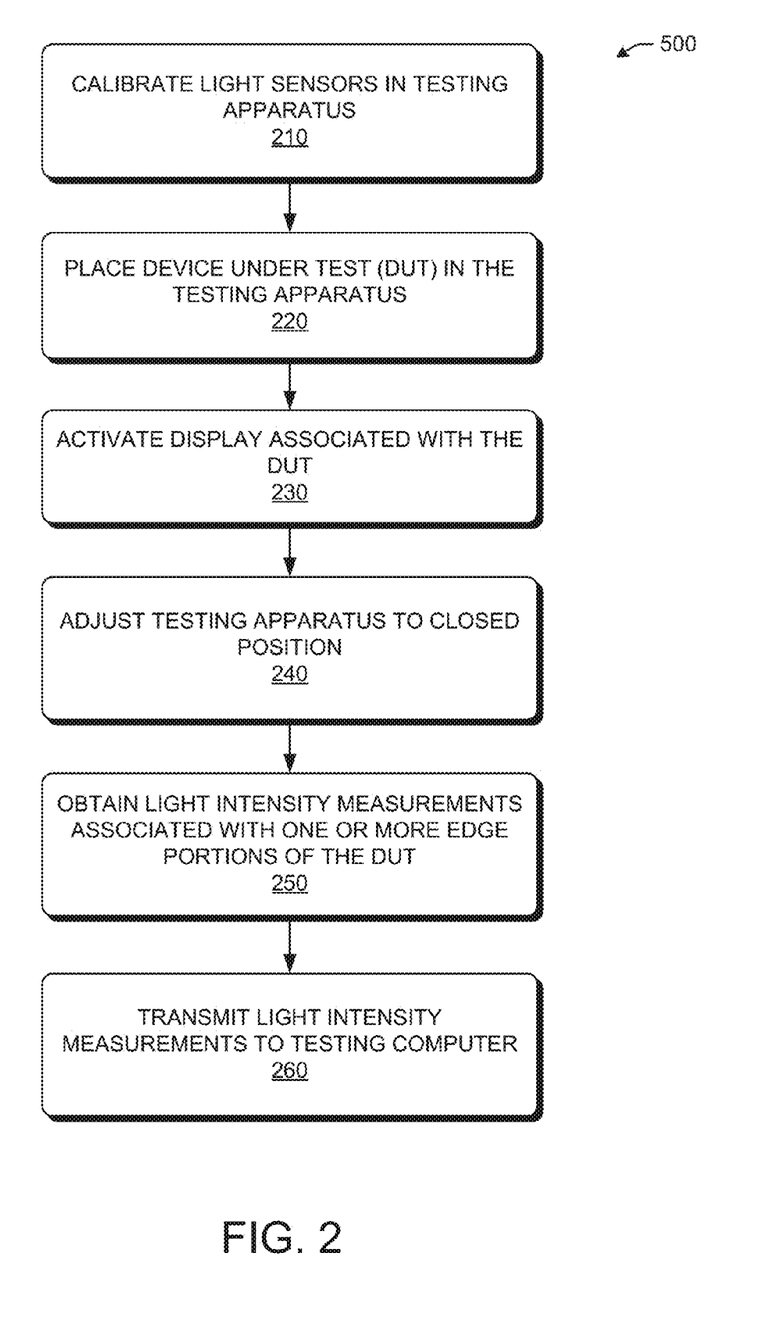
FIG. 2 illustrates a flow diagram for detecting light leakage in a device in accordance with one or more embodiments of the disclosure.

Referring now to FIG. 2, a flow diagram of a method 200 for detecting light leakage in a device is illustrated according to one or more example embodiments. The method 200 may begin in block 210 where a testing apparatus (e.g., testing apparatus 101) may be calibrated. For example, one or more light sensors coupled to the testing apparatus may be calibrated such that light intensity measurements obtained by the light sensors are consistent across the light sensors.

In block 220, a DUT (e.g., DUT 102) may be placed in and/or otherwise coupled to the testing apparatus. In block 230, a display associated with the DUT may be activated. In certain implementations, a tester may manually activate the display. In other implementations, the display may be automatically activated upon placing the DUT in the testing apparatus. In block 240, the testing apparatus may be adjusted to a closed position. For instance, a tester may pull down a lid member of the testing apparatus to rest on top of a base portion of the testing apparatus. While in the closed position, ambient light from an environment in which the testing apparatus is located may be prevented from entering the testing apparatus.

In block 250, the testing apparatus may obtain light intensity measurements associated with one or more edge portion of the DUT. For instance, the one or more light sensors may be configured to receive light emanating from the display of the DUT. In block 260, the light intensity measurements may be transmitted to a testing computer (e.g., testing computer 218).

Figure 3:
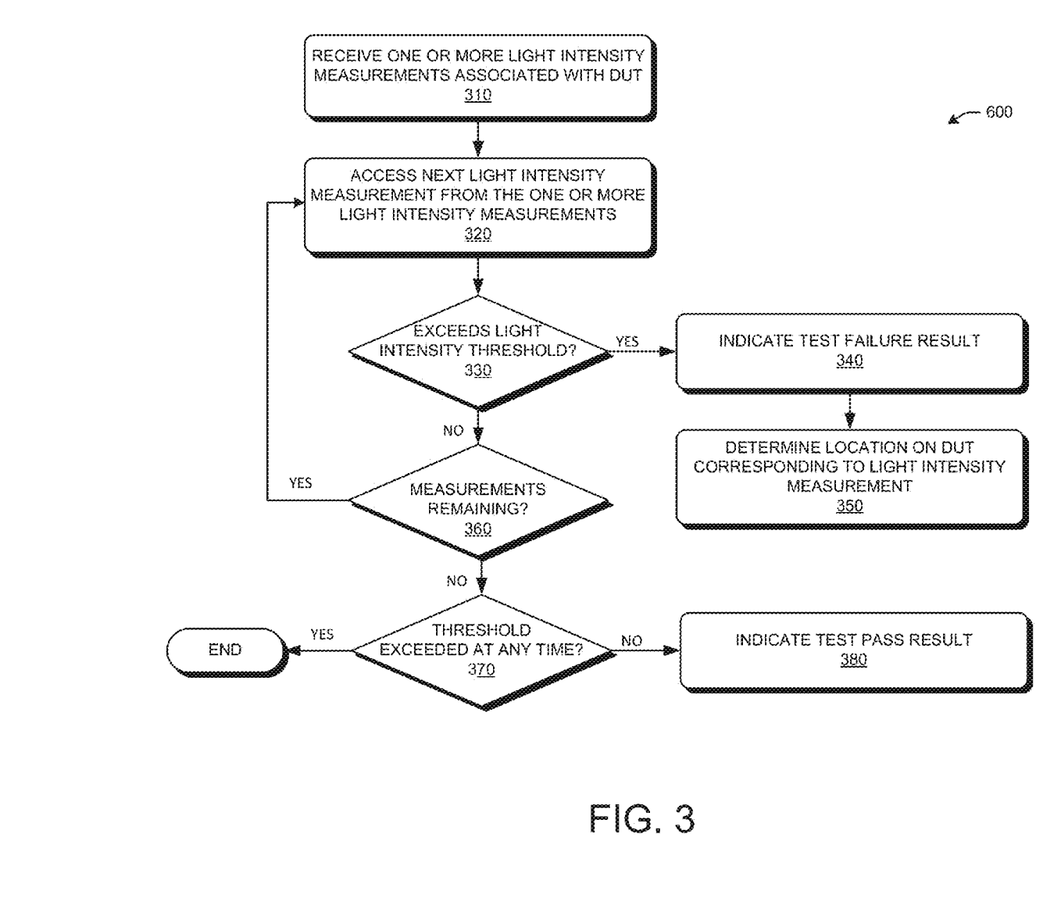
FIG. 3 illustrates another flow diagram for detecting light leakage in a device in accordance with one or more embodiments of the disclosure.

Referring now to FIG. 3, a flow diagram of a method 300 for detecting light leakage in a device is illustrated according to one or more example embodiments. The method 300 may begin in block 310 where a testing computer may receive one or more light intensity measurements associated with a DUT (e.g., DUT 102). In block 320 the testing computer may access the next light intensity measurement from the received one or more light intensity measurements (e.g., received from a testing apparatus, such as testing apparatus 101).

In diamond 330, the testing computer may determine whether the next light intensity measurement exceeds a light intensity threshold. If so, the method 300 may proceed to block 340 in which the testing computer may indicate a test failure result (e.g., via a display on the testing computer). In block 350, the testing computer may determine a location along an edge portion of the DUT that corresponds to the light intensity measurement that exceeded the light intensity threshold.

Referring back to diamond 330, if the testing computer determines that the next lighting intensity measurement does not exceed the light intensity threshold, the testing computer may proceed to diamond 360. In diamond 360, the testing computer may determine whether there are any light intensity measurements remaining out of the received one or more light intensity measurements. If so, the method 300 may return back to block 320 and repeat the process starting from block 320. If there are no light intensity measurements remaining, the method may proceed to diamond 370. In diamond 370, the testing computer may determine whether the light intensity threshold was exceeded at any time by any of the received one or more light intensity measurements. If so, the method 300 may end. If not, the method 300 may proceed to block 380, in which a testing computer may indicate a test pass result.

It will be appreciated that the method 300 depicted in FIG. 3 is for illustrative purposes only, and that other methods are also possible for determining light leakage in a DUT 102. For instance, multiple different light intensity thresholds may be compared with received light intensity measurements. Furthermore, various other criteria may be used to determine test failure results and/or test pass results. For example, test failure and/or test pass results may depend on a number of light intensity thresholds that are exceeded, as will be described in more detail below.

Figure 4A:
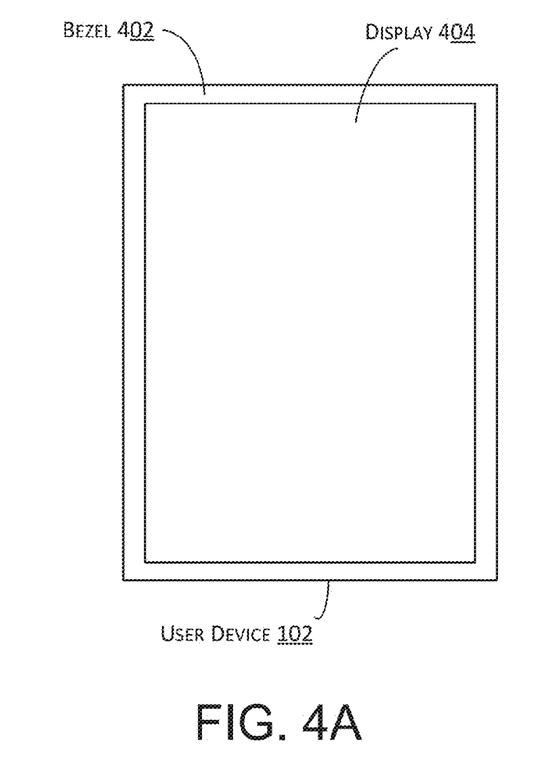
FIG. 4A illustrates a schematic front view diagram of a device under test in accordance with one or more embodiments of the disclosure.
Figure 4B:
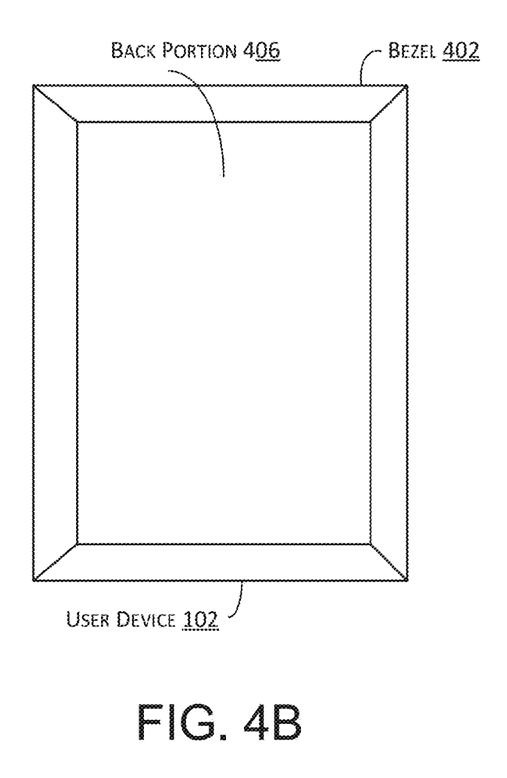
FIG. 4B illustrates a schematic back view diagram of a device under test in accordance with one or more embodiments of the disclosure.

Referring now to FIG. 4A and FIG. 4B, schematic diagrams are illustrated for a DUT 102 in accordance with one or more example embodiments. In particular, FIG. 4A illustrates a front view of the DUT 102 while FIG. 4B illustrates a back view of the DUT 102 As shown in both figures, the DUT 102 may include a bezel 402 coupled to a display 404. Furthermore, the bezel 402 may form seamlessly into the back portion 406 of the DUT 102.

In certain embodiments, the display 404 may be set in or otherwise coupled to the bezel 402 and/or back portion 406 of the DUT 102. For example, the display 404 may be glued to the bezel 402 and/or back portion 406. It will be appreciated that any other coupling means (e.g., using screws or other fastening components) are also possible. In certain cases, a defect may exist with respect to the coupling of the display 404 to the bezel 402 and/or back portion 406. As a result of the defect, light emitted from the display may leak out between the bezel 402 and the display 404.

Figure 5:
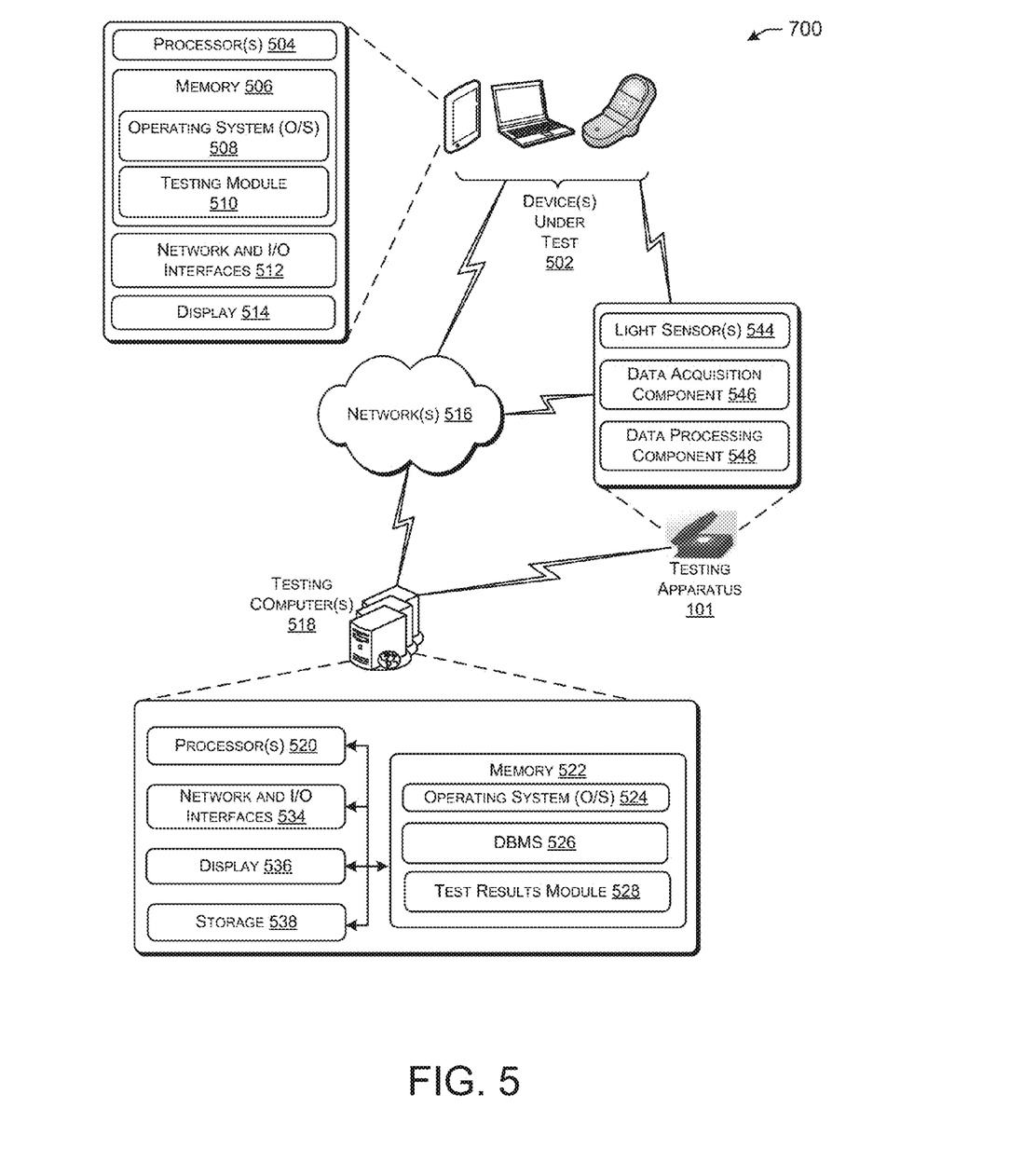
FIG. 5 illustrates a system for detecting light leakage in a device in accordance with one or more embodiments of the disclosure.

With reference now to FIG. 5, a system 500 for detecting light leakage in a device is shown according to one or more embodiments of the disclosure. The system 500 may include one or more DUTs 502. In certain implementations, the DUT 502 may correspond to the DUT 102 illustrated in FIGS. 1A-1C. The DUT 502 may include one or more computer processors 504, a memory 506 storing an operating system 508 and a test module 510, network and I/O interfaces 512, and a display 514. In certain embodiments, the DUT 502 may include one or more sensors capable of gathering information associated with a present environment of the DUT 502, or similar hardware devices, such as a camera, microphone, antenna, or Global Positioning Satellite (GPS) device.

The computer processors 504 may comprise one or more cores and may be configured to access and execute (at least in part) computer-readable instructions stored in the memory 506. The one or more computer processors 504 may include, without limitation: a central processing unit (CPU), a digital signal processor (DSP), a reduced instruction set computer (RISC), a complex instruction set computer (CISC), a microprocessor, a microcontroller, a field programmable gate array (FPGA), or any combination thereof. The DUT 502 may also include a chipset (not shown) for controlling communications between the one or more processors 504 and one or more of the other components of the DUT 502. The one or more processors 504 may also include one or more application-specific integrated circuits (ASICs) or application-specific standard products (ASSPs) for handling specific data processing functions or tasks.

The memory 506 may comprise one or more computer-readable storage media (CRSM). In some embodiments, the memory 506 may include non-transitory media such as random access memory (RAM), flash RAM, magnetic media, optical media, solid state media, and so forth. The memory 506 may be volatile (in that information is retained while providing power) or non-volatile (in that information is retained without providing power). Additional embodiments may also be provided as a computer program product including a transitory machine-readable signal (in compressed or uncompressed form). Examples of machine-readable signals include, but are not limited to, signals carried by the Internet or other networks. For example, distribution of software via the Internet may include a transitory machine-readable signal. Additionally, the memory 506 may store an operating system 508 that includes a plurality of computer-executable instructions that may be implemented by the computer processor to perform a variety of tasks to operate the interface(s) and any other hardware installed on the DUT 502. The operating system 508 may include any operating system now known or which may be developed in the future including, but not limited to, any server operating system, any mainframe operating system, or any other proprietary or freely available operating system. The memory 506 may also store content that may be displayed by the DUT 502 or transferred to other devices (e.g., headphones) to be displayed or played by the other devices. The memory 506 may also store content received from the other devices. The content from the other devices may be displayed, played, or used by the DUT 502 to perform any necessary tasks or operations that may be implemented by the computer processor or other components in the DUT 502.

Furthermore, the memory 506 may store a testing module 510 to facilitate testing of the DUT. For instance, the testing module 510 may be configured to adjust, based on user input, one or more display settings associated with a display 514. Such adjustments may include increasing and/or decreasing the brightness or light intensity produced by the display 514.

The network and I/O interfaces 512 may also comprise one or more communication interfaces or network interface devices to provide for the transfer of data between the DUT 502 and another device (e.g., network server) via a network (not shown). The communication interfaces may include, but are not limited to, personal area networks (PANs), wired local area networks (LANs), wireless local area networks (WLANs), wireless wide area networks (WWANs), and so forth. The DUT 502 may be coupled to the network via a wired connection. However, the wireless system interfaces may include the hardware and software to broadcast and receive messages either using the Wi-Fi Direct Standard (see Wi-Fi Direct specification published in Oct. 2010) and/or the IEEE 802.11 wireless standard (see IEEE 802.11-2007, published Mar. 8, 2007; IEEE 802.11n-2009, published Oct. 2009), or a combination thereof. The wireless system (not shown) may include a transmitter and a receiver or a transceiver (not shown) capable of operating in a broad range of operating frequencies governed by the IEEE 802.11 wireless standards. The communication interfaces may utilize acoustic, radio frequency, optical, or other signals to exchange data between the DUT 502 and another device such as an access point, a host computer, a server, a router, a reader device, and the like. The network may include, but is not limited to: the Internet, a private network, a virtual private network, a wireless wide area network, a local area network, a metropolitan area network, a telephone network, and so forth. In addition, the network and I/O interfaces 512 may include one or more peripheral devices to interface with a user. For instance, such devices may include mouses, keyboards, microphones, cameras, webcams, speakers, and/or the like.

The display 514 may include, but is not limited to, a liquid crystal display, a light-emitted diode display, an E-Ink™ display as made by E Ink Corp. of Cambridge, Mass., or any other similar type of output device. The display 514 may be used to show content to a user in the form of text, images, or video. In certain instances, the display 514 may also operate as a touch screen display that may enable the user to initiate commands or operations by touching the screen using certain finger or hand gestures.

According to one or more embodiments, the DUT 502 may be in communication, via one or more networks 516, with one or more testing computer(s) 518. As used herein, unless otherwise specified, the term "server" may refer to any computing device having a networked connectivity and configured to provide one or more dedicated services to clients, such as a DUT 502. The services may include storage of data or any kind of data processing.

As such, the testing computer(s) 518 may include one or more processors 520 and a memory 522. The memory 522 may store an operating system 524, a database management system (DBMS) 526, and a test results module 528. In addition, the testing computer(s) 518 may also include network and I/O interfaces 534, a display 536, and a storage 538. Furthermore the DBMS 526 may be in communication with a service provider datastore 540. While any of the above mentioned components in the DUT 502 and the testing computer (s) 518 may hereinafter be referred to in the singular, it will be appreciated that any future references to these components also contemplate them in a plurality.

The processors 520 may comprise one or more cores and may be configured to access and execute (at least in part) computer-readable instructions stored in the memory 522. The one or more computer processors 520 may include, without limitation (and similarly to the processors 504 in the DUT 502), a CPU, DSP, RISC, CISC, a microprocessor, a microcontroller, a field programmable gate array (FPGA), or any combination thereof. The testing computer 518 may also include a chipset (not shown) for controlling communications between the one or more processors 520 and one or more of the other components of the testing computer 518. In certain embodiments, the testing computer 518 may be based on an Intel® architecture or an ARM® architecture, and the processor(s) and chipset may be from a family of Intel® processors and chipsets. The one or more processors 520 may also include one or more application-specific integrated circuits (ASICs) or application-specific standard products (ASSPs) for handling specific data processing functions or tasks.

The memory 522 may comprise one or more computer-readable storage media (CRSM). Similar to the memory 506 in the DUT 502, the memory 522 may include non-transitory media such as RAM, flash RAM, magnetic media, optical media, solid state media, and so forth. The memory 522 may be volatile or non-volatile and may also be provided as a computer program product including a transitory machine-readable signal (in compressed or uncompressed form). Additionally, the memory 522 may store an operating system 524 that includes a plurality of computer-executable instructions that may be implemented by the computer processor to perform a variety of tasks to operate the interface(s) and any other hardware installed on the testing computer 518. The operating system 524 may include any operating system now known or which may be developed in the future including, but not limited to, any server operating system, any mainframe operating system, or any other proprietary or freely available operating system.

It should be appreciated that any data and/or computer-executable instructions stored in the memory 522 may be additionally, or alternatively, stored in the data storage 538 and/or in one or more other datastores. The DBMS 526 depicted as being loaded into the memory 522 may support functionality for accessing, retrieving, storing, and/or manipulating data stored in external datastore(s) (e.g., the service provider datastore(s) 540), data stored in the memory 522, and/or data stored in the data storage 538. For example, the DBMS 526 may be configured to retrieve user account data (e.g., information related to items, media files, users, feedback data, etc.) from service provider datastore(s) 540 responsive to receipt of the request from the testing computer 518. The DBMS 526 may use any of a variety of database models (e.g., relational model, object model, etc.) and may support any of a variety of query languages.

The network and I/O interfaces 534 may also comprise one or more communication interfaces or network interface devices to provide for the transfer of data between the testing computer 518 and another device (e.g., network server) via a network (not shown). The communication interfaces may include, but are not limited to, personal area networks (PANs), wired local area networks (LANs), wireless local area networks (WLANs), wireless wide area networks (WWANs), and so forth. As such, the testing computer 518 may be coupled to the network via a wired connection and/or a wireless connection. The communication interfaces may utilize acoustic, radio frequency, optical, or other signals to exchange data between the testing computer 518 and another device such as an access point, a host computer, a server, a router, a reader device, and the like. The network may include, but is not limited to, the Internet, a private network, a virtual private network, a wireless wide area network, a local area network, a metropolitan area network, a telephone network, and so forth.

The display 536 may include, but is not limited to, a liquid crystal display, a light-emitted diode display, an E-Ink™ display as made by E Ink Corp. of Cambridge, Mass., or any other similar type of output device. The display 536 may be used to show content to a user in the form of text, images, or video. In certain instances, the display 536 may also operate as a touch screen display that may enable the user to initiate commands or operations by touching the screen using certain finger or hand gestures.

The testing computer 518 may further comprise storage 538, such as removable storage and/or non-removable storage including, but not limited to, magnetic storage, optical disk storage, and/or tape storage. Storage 538 may provide non-transient storage of computer-executable instructions and other data. The storage 538 may include storage that is internal and/or external to the user testing computer 518.

According to one or more embodiments, the DUT 502 and the testing computer 518 may also be in communication with a testing apparatus 542. For instance, the testing apparatus 542 may be configured to receive the DUT 502 (e.g., a tester may place the DUT on to the testing apparatus 542). In some implementations, the testing apparatus 542 may be of a clam shell design although other shapes and/or structures are also possible. The testing apparatus may also include one or more light sensors 544 configured to determine, obtain, receive, and/or otherwise provide for one or more light intensity measurements associated with light leakage from the DUT 502.

Additionally, the DUT 502 may also include a data acquisition component 546. The data acquisition component 546 may be configured to receive the light intensity measurements from the light sensor(s) 544. Furthermore, the data acquisition component 546 may be configured to transmit the light intensity measurements to the testing computer(s) 518 (e.g., to the test results module 528). In certain implementations, the data acquisition component 546 may include circuitry that directly communicates with the testing computer 518 (e.g., via a universal serial bus (USB) port and/or USB cable). In other implementations, the data acquisition component 546 may be configured to communicate with the testing computer (s) 518 via the one or more networks 516.

In addition, the test results module 528, included in the testing computer 518, may detect and/or otherwise determine, based at least in part on the light intensity measurements received from the testing apparatus 542, whether any light leakage is present with respect to the DUT 502. For instance, the test results module 528 may be configured to determine whether the one or more light intensity measurements exceed a light intensity threshold. In some implementations, if any of the light intensity measurements is greater than or equal to the light intensity threshold, the test results module may be configured display and/or otherwise indicate a failure of a light leakage test. Conversely, if all of the light intensity measurements are less than the light intensity threshold, the test results module 528 may be configured display and/or otherwise indicate a success or passing of the light leakage test. It will be appreciated that in other implementations, success or failure of the light leakage test may depend on other factors, such as a number of light intensity measurements that pass or fail the light leakage test.

According to one or more embodiments, upon determination of a test failure, the test results module 528 may also be configured to determine a location of light leakage with respect to the DUT 502. For instance, each of the light sensor (s) 544 included in the testing apparatus may generate and/or provide a respective light intensity measurement. To this end, the data acquisition component 546 may be configured to transmit light sensor identifier information associated with respective light intensity measurements to the test results module 528. The light sensor identifier information may indicate, for each respective light intensity measurement, the corresponding light sensor 544 that obtained and/or produced the light intensity measurement. For instance, the test results module 528 may identify a particular light intensity measurement that exceeds a light intensity threshold. Based at least in part on the light sensor identifier information associated with the particular light intensity measurement, the test results module 528 may identify a corresponding light sensor 544. In certain implementations, the light sensor(s) 544 may also be associated with respective positional identifiers. The positional identifiers may indicate, for the respect light sensors 544, a location of the light sensors 544 on testing apparatus 101 and/or with respect to the DUT 502. Furthermore, based on the location of the identified light sensor 544 in relation to the DUT 502, the test results module 528 may determine the location of light leakage along the DUT 502 itself.

For instance, the test results module 528 may determine that a particular light intensity measurement is greater than a light intensity threshold. Based on sensor identifier associated with the light intensity measurement, the test results module 528 may identify the light sensor 544 corresponding to the light intensity measurement. Furthermore, based at least in part on a positional identifier associated with the light sensor 544, the test results module 528 may determine a location of the light sensor 544. For example, the test results module 528 may determine that the light sensor 544 is located opposite a top edge portion of the DUT 502. As a result, the test results module 528 may determine that light leakage is present along the top edge portion of the DUT 502.

It will be appreciated that various other testing algorithms are also possible for detecting the presence of light leakage with respect to the DUT 502. For instance, the test results module 528 may be configured to apply different light intensity thresholds based on a brightness level associated with the display 514 of the DUT 502. To this end, a greater brightness level of the display 514 may correspond to the test results module 528 applying a greater light intensity threshold to any obtained light intensity measurements by the light sensors 544.

As another example, the test results module 528 may also apply different light intensity thresholds based on the proximity of light sensors 544 to each other. For instance, if two light sensors 544 are within a predetermined distance from each other, the test results module 528 may apply a first light intensity threshold to the sum of respective light intensity measurements provided by the two light sensors 544. If the same two light sensors 544 were located further apart than the predetermined distance, the test results module 528 may individually apply a second, different light intensity threshold to each of the two light sensors 544.

In yet other implementations, the test results module 528 may also apply different light intensity thresholds depending on one or more colors of light emitted by the display 514 of the DUT 502. For instance, white light may be associated with a different light intensity threshold than blue light.

Furthermore, in some embodiments, the testing apparatus 542 may include a data processing component 548 configured to perform one or more of the operations described above with respect to the test results module 528 of the testing computer 518. In these embodiments, the testing apparatus 542 itself may be configured to indicate test results (e.g., such as via a display) with respect to light leakage tests conducted on the DUT 502.

It will be further appreciated that while FIG. 5 illustrates the testing computer 518 as including various modules, in other embodiments, such modules may be dispersed among different devices in communication with each other. In some implementations, the functionality described with respect to the testing computer 518 may also be performed at least in part by the DUT 502 and/or the testing apparatus 542.

Figure 6:
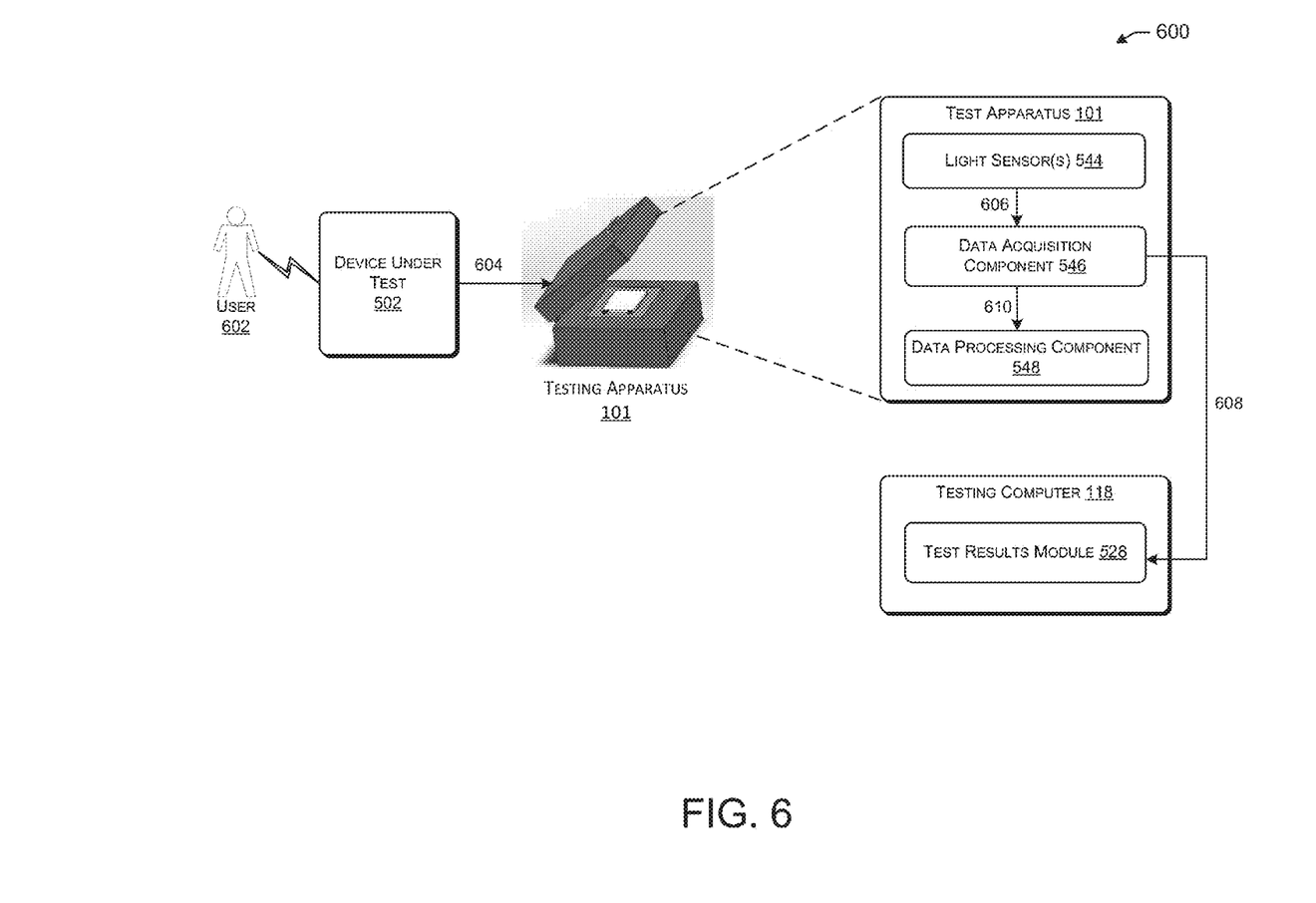
FIG. 6 illustrates a data flow diagram for detecting light leakage in a device in accordance with one or more embodiments of the disclosure.

Referring now to FIG. 6, a block diagram of a data flow 600 for detecting light leakage in a device is illustrated in accordance with one or more example embodiments. According to the data flow 600, a user 602 may place 604 a DUT 502 into or onto a testing apparatus 101. In some implementations, the user may also activate the display 514 of the DUT 502. In other implementations, the display 514 may be activated upon the DUT 502 being placed into/onto the testing apparatus 542. Furthermore, the user 602 may adjust the testing apparatus 542 to a closed position.

Upon being closed, the light sensors 544 included in the testing apparatus 542 may be configured to obtain and/or receive one or more light intensity measurements along one or more edge portions of the DUT 502. The light sensors 544 may then be configured to provide 606 the one or more light intensity measurements to a data acquisition component 546. Upon receipt, the data acquisition component 546 may be configured to transmit 608 the one or more light intensity measurements to a tests results module 528 of a testing computer 518. To this end, the test results module 528 may be configured to determine, based at least in part on the one or more light intensity measurements, whether light leakage is present along the one or more edge portions of the DUT 502.

In certain implementations, the data acquisition component 546 may also be configured to transmit the one or more light intensity measurements to the data processing component 548. As previously discussed, the data processing component 548 may be configured to perform one or more of the operations performed by the test results module 528.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

These computer-executable program instructions may be loaded onto a special-purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable storage media or memory that can direct a computer or other programmable data processing apparatus to function in a particular manner, such that the instructions stored in the computer-readable storage media produce an article of manufacture including instruction means that implement one or more functions specified in the flow diagram block or blocks. As an example, certain implementations may provide for a computer program product, comprising a computer-readable storage medium having a computer-readable program code or program instructions implemented therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language is not generally intended to imply that features, elements, and/or operations are in any way required for one or more implementations or that one or more implementations necessarily include logic for deciding, with or without user input or prompting, whether these features, elements, and/or operations are included or are to be performed in any particular implementation.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense only and not for purposes of limitation.

The invention claimed is:

1. A system, comprising:
a base portion comprising a device receptacle component, wherein the device receptacle component is to receive a device under test (DUT), the DUT comprising a bezel element coupled to a display element;
an array of light sensors coupled to the base portion, wherein the array of light sensors is positioned at a predetermined distance from a first edge portion of the DUT when the DUT is placed in the device receptacle component;
a lid member pivotally coupled to an edge of the base portion, wherein the lid member is adjustable to prevent light from illuminating the DUT when the lid member is placed over the base portion;
at least one processor; and
at least one memory storing computer-executable instructions, that when executed by the at least one processor, causes the at least one processor to:
receive, from the array of light sensors, a plurality of light intensity measurement values corresponding to a portion of light emitted by the display element, the portion of light being light leaking out between the bezel element and the display element along the first edge portion of the DUT;
and
transmit the plurality of light intensity measurement values to a testing computer, wherein the plurality of light intensity measurements comprise respective lux values.

2. The system of claim 1, wherein the computer-executable instructions further cause the at least one processor to:
receive, from the testing computer in response to the transmitted light intensity measurement values, an indication that the portion of the light leaking out between the bezel element and the display element of the DUT is within an unacceptable range, wherein the indication is based at least in part on a determination that at least one light intensity measurement value of the plurality light intensity measurement values is greater than a light intensity threshold.

3. The system of claim 1, wherein the computer-executable instructions further cause the at least one processor to:
receive, from the testing computer in response to the transmitted light intensity measurement values, an indication that the portion of the light leaking out between the bezel element and the display element of the DUT is within an acceptable range, wherein the indication is based at least in part on a determination that the plurality light intensity measurement values are respectively less than a light intensity threshold.

4. The system of claim 1, wherein the array of light sensors is movable or rotatable along at least one of an x-axis, y-axis, or z-axis.

5. A method, comprising:
providing a testing apparatus with a device under test (DUT) coupled to the testing apparatus, wherein the testing apparatus includes a light sensor positioned at a first predetermined distance from a first edge portion of the DUT when the DUT is coupled to the testing apparatus;
causing, by the testing apparatus, a light source associated with a display of the DUT to be activated when the DUT is coupled to the testing apparatus;
receiving, by the light sensor, a portion of light emitted by the light source, wherein the portion of the light corresponds to light leakage between the display element and a bezel element of the DUT along a first edge portion of the DUT;
determining, by the light sensor, a first light intensity measurement value corresponding to the portion of the light; and
transmitting, by the testing apparatus, the first light intensity measurement value to a testing computer.

6. The method of claim 5, further comprising:
receiving, from the testing computer in response to the transmitted first light intensity measurement value, an indication that the light leakage is within an unacceptable range, wherein the indication is based at least in part on a determination that the first light intensity measurement value is greater than a light intensity threshold.

7. The method of claim 6, further comprising:
determining, based at least in part on a sensor identifier associated with the light sensor, a location of the light sensor with respect to the DUT; and
determining, based at least in part on the location of the light sensor, a location of the light leakage.

8. The method of claim 5, wherein the testing apparatus further includes a plurality of light sensors, the plurality of light sensors comprising the light sensor, and wherein the method further comprises:
receiving, by the plurality of light sensors, the portion of the light emitted by the light source;
determining, by the plurality of light sensors, a plurality of light intensity measurement values corresponding to the portion of light, wherein the plurality of light intensity measurement values comprises the first light intensity measurement value;
transmitting, by the testing apparatus, the plurality of light intensity measurement values to the testing computer; and
receiving, from the testing computer in response to the transmitted light intensity measurement values, an indication that the light leakage is within an acceptable range, wherein the indication is based at least in part on a determination that the plurality light intensity measurement values are respectively less than a light intensity threshold.

9. The method of claim 5, further comprising:
determining, by a second light sensor coupled to the base portion, a second light intensity measurement value associated with the portion of the light;
transmitting, by the testing apparatus, the second light intensity measurement to the testing computer; and receiving, from the testing computer, an indication that the light leakage is within an unacceptable range, wherein in the indication is based at least in part on a determination that the first light sensor and the second light sensor are positioned within a second predetermined distance from each other and that a sum of the first light intensity measurement value and the second light intensity measurement value is greater than a light intensity threshold.

10. The method of claim 9, wherein the first light sensor and the second light sensor are included in an array of light sensors.

11. The method of claim 5, wherein the testing apparatus further includes a second light sensor positioned at a second predetermined distance from a second edge portion of the DUT when the DUT is coupled to the testing apparatus, wherein the method further comprises:
determining, by the second light sensor, a second light intensity measurement value corresponding to the portion of the light; and
transmitting, by the testing apparatus, the second light intensity measurement value to the testing computer.

12. The method of claim 11, further comprising:
receiving, from the testing computer in response to the transmitted second light intensity measurement value, an indication that the light leakage is within an unacceptable range, wherein the indication is based at least in part on a determination that the second light intensity measurement value is greater than a light intensity threshold.

13. A testing apparatus, comprising:
a base portion configured to couple to a device under test (DUT);
a top portion configured to couple to the base portion;
one or more light sensors coupled to the top portion, wherein the one or more light sensors are positioned at a first predetermined distance from a first edge portion of the DUT when the DUT is coupled to the base portion and the top portion is coupled to the base portion; and
a data processing component configured to:
receive, from the one or more light sensors, one or more light intensity measurement values associated with a portion of light emitted by a display element of the DUT, wherein the portion of the light corresponds to light leaking out between the display element and a bezel element of the DUT along the first edge portion of the DUT; and
determine, based at least in part on the one or more light intensity measurement values, whether the portion of light leaking out between the display element and the bezel element is within an acceptable range or an unacceptable range.

14. The testing apparatus of claim 13, wherein the data processing component is further configured to:
determine that at least one light intensity measurement value from the one or more light intensity measurements is greater than a light intensity threshold; and
generate an indication that the portion of the light leaking out between the display element and the bezel element is within the unacceptable range.

15. The testing apparatus of claim 14, wherein each of the one or more lights sensors is associated with a positional identifier indicating respective position of each of the one or more light sensors in relation to the first edge portion of the DUT.

16. The testing apparatus of claim 15, wherein the data processing component is further configured to:

identify, based at least in part on at least one sensor identifier associated with the at least one light intensity measurement value, at least one light sensor from the one or more light sensors;

determine at least one positional identifier, from the one or more positional identifiers, associated with the least one light sensor;

determine, based at least in part on the at least one positional identifier, a position of the at least one light sensor relative to the first edge portion of the DUT; and identify, based at least in part on the position of the at least one light sensor, a location of the portion of the light leaking out between the bezel element and the display element along the first edge portion of the DUT.

17. The testing apparatus of claim 13, wherein the data processing component is further cause configured to:

determine that the one or more light intensity measurement values are respectively less than a light intensity threshold;

generate an indication the portion of the light leaking out between the display element and the bezel element is within the acceptable range.

18. The testing apparatus of claim 13, wherein the top portion is adjustable to prevent exposure of the DUT to ambient light when the top portion is placed over the base portion.

19. The testing apparatus of claim 13, wherein the testing apparatus further comprises a fastening component coupled to the base portion, wherein the fastening component is to secure the DUT to the base portion.

20. The testing apparatus of claim 13, wherein the one or more light sensors are included in an array of light sensors.

* * * * *